(12) United States Patent
Meir et al.

(10) Patent No.: US 10,828,512 B2
(45) Date of Patent: Nov. 10, 2020

(54) PATIENT MONITORING SYSTEM

(71) Applicant: VISION RT LIMITED, London (GB)

(72) Inventors: Ivan Daniel Meir, London (GB); Adrian Roger William Barrett, London (GB)

(73) Assignee: Vision RT Limited, London (GB)

( * ) Notice: Subject to any disclaimer, the term of this patent is extended or adjusted under 35 U.S.C. 154(b) by 190 days.

(21) Appl. No.: 16/002,893

(22) Filed: Jun. 7, 2018

(65) Prior Publication Data

US 2018/0353774 A1    Dec. 13, 2018

(30) Foreign Application Priority Data

Jun. 7, 2017    (GB) .................... 1709093.7

(51) Int. Cl.
*A61N 5/10* (2006.01)
*G06K 9/62* (2006.01)
*G16H 40/63* (2018.01)
*G16H 50/50* (2018.01)
*G16H 30/40* (2018.01)
(Continued)

(52) U.S. Cl.
CPC .......... *A61N 5/1049* (2013.01); *A61N 5/107* (2013.01); *A61N 5/1039* (2013.01); *A61N 5/1047* (2013.01); *A61N 5/1081* (2013.01); *G16H 20/40* (2018.01); *G16H 30/40* (2018.01); *G16H 40/63* (2018.01); *G16H 50/20* (2018.01); *G16H 50/50* (2018.01); *A61B 2034/105* (2016.02); *A61B 2090/3937* (2016.02); *A61N 5/1069* (2013.01); *A61N 2005/1059* (2013.01)

(58) Field of Classification Search
CPC ...... A61B 2034/105; A61B 2090/3937; A61N 2005/1059; A61N 5/1039; A61N 5/1047; A61N 5/1049; A61N 5/1069; A61N 5/107; A61N 5/1081; G16H 20/40; G16H 30/40; G16H 40/63; G16H 50/20; G16H 50/50
See application file for complete search history.

(56) References Cited

U.S. PATENT DOCUMENTS 7,348,974 B2    3/2008    Smith et al.
7,889,906 B2    2/2011    Smith et al.
(Continued)

OTHER PUBLICATIONS

Combined Search and Examination Report for British Patent App. No. 1709093.7 (dated Dec. 14, 2017).
(Continued)

*Primary Examiner* — Nirav G Patel
(74) *Attorney, Agent, or Firm* — Birch, Stewart, Kolasch & Birch, LLP

(57) ABSTRACT

Some embodiments are directed to a monitoring system for monitoring the positioning of a patient relative to a treatment apparatus operable to deliver radiation along a radiation path. A model generation module is arranged to generate a model of a surface of a patient being monitored. A comparison module determines a transformation required to match the generated model to the stored model target surface. An offset determination module then utilizes the transformation and data indicative of a current position of a treatment apparatus to determine an offset value indicative of the offset of the surface of a patient relative to an axis corresponding to a determined current radiation path for radiation generated by the treatment apparatus applied to a patient. If the offset value exceeds a threshold, a warning may be generated or treatment may be halted.

16 Claims, 7 Drawing Sheets

(51) Int. Cl.
*G16H 20/40* (2018.01)
*G16H 50/20* (2018.01)
 A61B 34/10 (2016.01)
 A61B 90/00 (2016.01)

(56) References Cited

U.S. PATENT DOCUMENTS

| | | |
|---|---|---|
| 2008/0049896 A1 | 2/2008 | Kuduvalli |
| 2015/0265852 A1 | 9/2015 | Meir et al. |
| 2015/0360054 A1 | 12/2015 | Jeong |
| 2016/0129283 A1 | 5/2016 | Meir et al. |

OTHER PUBLICATIONS

Extended European Search Report for European Patent App. No. 18175967 (dated Sep. 14, 2018).

PATIENT MONITORING SYSTEM

CROSS REFERENCE TO RELATED APPLICATIONS

This application claims priority to British Patent Application No.: GB1709093.7, filed on Jun. 7, 2017, the content of which is hereby incorporated in its entirety by reference.

BACKGROUND

Some embodiments relate to a patient monitoring system. More particularly, some embodiments relate to monitoring the positioning of patients and where appropriate generating a warning signal or halting treatment if a patient is found to have moved out of position. Some embodiments are particularly suitable for use with radiotherapy devices and the like where accurate positioning and the detection of patient movement improve or enhance successful treatment.

Radiotherapy can include or can consist of projecting onto a predetermined region of a patient's body, a radiation beam so as to destroy or eliminate tumors existing therein. Such treatment is usually carried out periodically and repeatedly. At each medical intervention, the radiation source must or should be positioned with respect to the patient to irradiate the selected region with the highest possible accuracy to avoid radiating adjacent tissue on which radiation beams would be harmful. If movement of a patient is detected the treatment should be halted to avoid irradiating areas of a patient other than a tumor location.

Related monitoring systems for assisting the positioning of patients and monitoring of patient movement during radiotherapy have previously been proposed, such as those described in Vision RT's earlier patents and patent applications U.S. Pat. Nos. 7,348,974, 7,889,906 and U.S. Patent Publication No. 2015-265852, all of which are hereby incorporated by reference. In the systems described in Vision RT's patent applications, stereoscopic images of a patient are obtained and processed to generate data identifying 3D positions of a large number of points corresponding to points on the surface of an imaged patient. Such data can be compared with data generated on a previous occasion and used to position a patient in a consistent manner or provide a warning when a patient moves out of position. Typically, such a comparison involves undertaking Procrustes analysis to determine a transformation which minimizes the differences in position between points on the surface of a patient identified by data generated based on live images and points on the surface of a patient identified by data generated on a previous occasion. When positioning a patient, the transformation can then be utilized to generate instructions for re-positioning the patient. During treatment, the transformation is used to identify when the patient is out of position and if a patient is out of position by more than a threshold amount, generate a warning and/or halt treatment.

SUMMARY

Determining an appropriate threshold for generating a warning or halting treatment is difficult. If the threshold is set at too low a level, treatment may be halted unnecessarily. Conversely setting too high a threshold may result in a radiation beam being misdirected with healthy tissue being irradiated by a treatment device rather than a tumor. Improvements in the manner of monitoring patients which address this issue are therefore desired.

Some embodiments therefore provide a monitoring system for monitoring the positioning of a patient relative to a treatment apparatus operable to deliver radiation along a radiation path, the monitoring system including: a model generation module operable to generate a model of a surface of the patient being monitored; a target model store operable to store a model of a target surface; a comparison module operable to determine a transformation required to match a model of the surface of the patient generated by the model generation module with a model of the target surface stored in the target model store; and an offset determination module operable to utilize the transformation determined by the comparison module and data indicative of a current position of the treatment apparatus to determine an offset value indicative of the offset of the surface of the patient relative to an axis corresponding to a determined current radiation path for radiation generated by the treatment apparatus applied to the patient.

In some embodiments the offset value may include a value indicative of the offset between the centroid of a generated model surface and a target surface in a direction normal to an axis corresponding to a current radiation path. In other embodiments, the offset value may include a value indicative of the degree of overlap between a target region and a generated radiation beam.

In some other embodiments the offset determination module may be arranged to utilize the determined transformation and data indicative of the current position of the treatment apparatus to model the passage of a radiation beam through the body of the patient to determine if the patient has moved out of position in a manner which is likely to be detrimental to the patient.

In some embodiments the monitoring system may be arranged to monitor the position and orientation of the treatment apparatus to determine the current radiation path of radiation generated by the treatment apparatus.

In some embodiments the monitoring system may be operable to receive data from a treatment apparatus wherein the monitoring system is arranged to determine the position and orientation of the treatment apparatus and determine a current radiation path of radiation generated by the treatment apparatus on the basis of received data. The data received from the treatment apparatus may include data identifying the position and orientation that the treatment apparatus has been instructed to adopt. Alternatively in other embodiments the treatment apparatus may include monitoring devices such as servos, stepper motors or motion detectors within the treatment apparatus for monitoring the positioning and orientation of the treatment apparatus.

Alternatively, in some other embodiments an axis corresponding to a current radiation path of radiation generated by the treatment apparatus may be inferred from a treatment plan identifying the positions and orientations from which a patient is to be irradiated.

In some embodiments the monitoring system may include a camera system operable to image the surface of a patient being monitored and the model generation module may be operable to process images obtained by the camera system to generate a model of the surface of the patient being monitored.

In some embodiments the camera system may be arranged to obtain images of the treatment apparatus and process the images to determine the orientation of an axis corresponding to a current radiation path.

In some embodiments, the camera system may include a camera system operable to image a pattern of light projected onto the surface of a patient. The light source in some such embodiments may include a laser light source and the projected pattern of light may include a pattern of infra-red light.

In some embodiments the pattern of light may include a speckle pattern and the camera system may include a stereoscopic camera system, wherein the model generation module may be arranged to generate models of surfaces appearing in images obtained by the camera system by identifying corresponding portions of a surface appearing in stereoscopic images obtained by the camera system onto which the speckle pattern is projected.

In some other embodiments the pattern of light may include structured light in the form of a line or grid or other predefined light pattern and the model generation module may be operable to generate models of surfaces appearing in images obtained by the camera system on the basis of the deformation of the pattern in images obtained by the camera system. Alternatively the camera system may include a time of flight camera system wherein the model generation module is operable to generate models of surfaces appearing in images obtained by the camera system on the basis of the timing of the capture of images of light reflected from the surfaces relative to the activation of the light source.

BRIEF DESCRIPTION OF THE DRAWINGS

Some embodiments of the presently disclosed subject matter will now be described in more detail with reference to exemplary embodiments, given by way of example, and with reference to the accompanying drawings, in which.

DETAILED DESCRIPTION OF EXEMPLARY EMBODIMENTS

A few inventive aspects of some embodiments are explained in detail below with reference to the various figures. Exemplary embodiments are described to illustrate the disclosed subject matter, not to limit its scope, which is defined by the claims. Those of ordinary skill in the art will recognize a number of equivalent variations of the various features provided in the description that follows.

Figure 1:
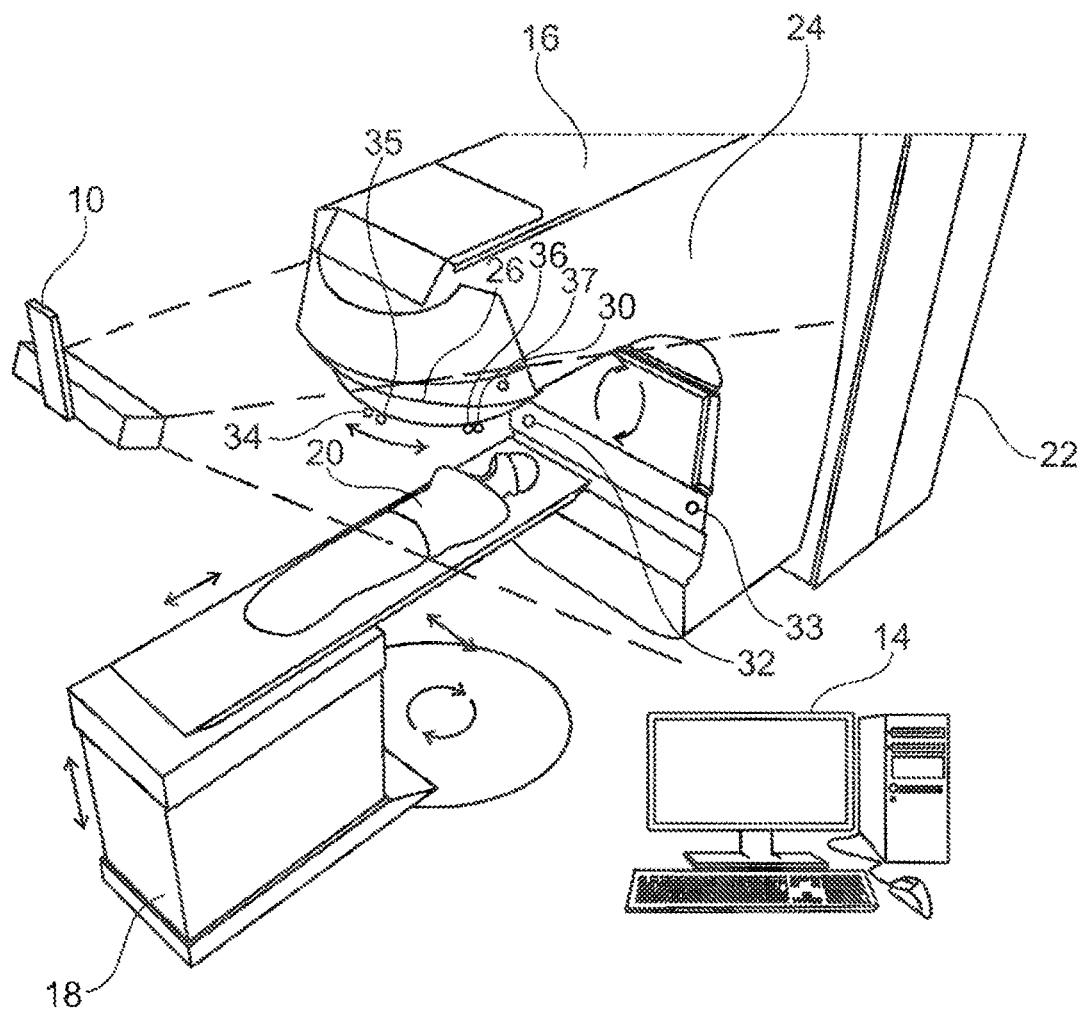
FIG. 1 is a schematic perspective view of a patient monitor in accordance with some embodiments in accordance with the presently disclosed subject matter.

FIG. 1 is a schematic perspective view of a patient monitor in accordance with some embodiments, wherein a set of stereoscopic cameras 10 is provided that are connected by wiring (not shown) to a computer 14. The computer 14 is also connected to treatment apparatus 16 such as a linear accelerator for applying radiotherapy. A mechanical couch 18 is provided as part of the treatment apparatus upon which a patient 20 lies during treatment. The treatment apparatus 16 and the mechanical couch 18 are arranged such that, under the control of the computer 14, the relative positions of the mechanical couch 18 and the treatment apparatus 16 may be varied, laterally, vertically, longitudinally and rotationally as is indicated in the figure by the arrows adjacent the couch.

The treatment apparatus 16 includes a main body 22 from which extends a gantry 24. A collimator 26 is provided at the end of the gantry 24 remote from the main body 22 of the treatment apparatus 16. To vary the angles at which radiation irradiates a patient 20, the gantry 24, under the control of the computer 14, is arranged to rotate about an axis passing through the center of the main body 22 of the treatment apparatus 16. Additionally, the location of irradiation by the treatment apparatus may also be varied by rotating the collimator 26 at the end of the gantry 24.

In use, the stereoscopic cameras 10 obtain video images of a patient 20 lying on the mechanical couch 18. These video images are passed via the wiring to the computer 14. The computer 14 then processes the images of the patient 20 to generate a model of the surface of the patient. This model is compared with a model of the patient generated during earlier treatment sessions. When positioning a patient the difference between a current model surface and a target model surface obtained from an earlier session is identified and the positioning instructions necessary to align the surfaces determined and sent to the mechanical couch 18.

Subsequently during treatment any deviation from an initial set up can be identified and if the deviation is greater than a threshold, the computer 14 sends instructions to the treatment apparatus 16 to cause treatment to be halted until a patient 20 can be repositioned.

It is not the case, however, that all or most movement will necessarily have a detrimental effect on the application of radiation to a treatment site. Motion which is aligned with the path of a radiation beam generated by a treatment apparatus 16 generally has little impact on the effectiveness of treatment since radiation is still applied to the treatment site. Rather, such movement merely has the effect of bringing a treatment site, closer or further away from a radiation source. In contrast, motion normal the path of a radiation beam can have a very significant effect as if such motion occurs, this can cause the radiation beam to fail to irradiate the treatment site and instead irradiate adjacent healthy tissue.

In these embodiments, in addition to monitoring a patient 20, the monitoring system also monitors the location and orientation of the gantry 24 and collimator 26 to determine a current orientation of the treatment apparatus 16 and thereby determine the orientation of a radiation beam applied to a patient 20 by the treatment apparatus 16. An offset measure identifying the extent to which a patient 20 has moved out of position in a manner which is likely to be detrimental to the patient 20 can then be calculated utilizing the determined orientation of a radiation beam and a calculated transform determined for matching the surface of a patient to a pre-stored target surface. This offset value can then be compared with a threshold to determine whether the motion of a patient is sufficient to justify generating a warning or halting treatment.

Thus in this way, rather than generating a warning or halting treatment on the basis of an absolute measure of patient motion, the monitoring system determines a measure relative to the orientation of the treatment apparatus 16 and hence the orientation of radiation applied to a patient by the treatment apparatus 16.

The monitoring of the relative positions of the treatment apparatus 16 and a patient 20 can be facilitated by providing a number of markers 30-37 attached to the surface of the main body of the treatment apparatus, the gantry 24, and the collimator 26 respectively. By providing the stereoscopic camera system 10 with an appropriate light source and making the markers reflective, it becomes possible to identify the portions of the images corresponding to the markers 30-37 by performing a thresholding operation. This enables the portions of images corresponding to the markers 30-37 to be rapidly identified. The processing of images to identify portions of images corresponding to the markers 30-37 can additionally be facilitated by using the expected or monitored positions of the treatment apparatus 16 to identify the expected portions of an image where markers 30-37 are expected to be viewed.

The positioning and format of the markers 30-37 need to be chosen to account for different portions of the treatment apparatus 16 being obscured at different times.

One suitable arrangement of markers 30-37 is to place the markers 30-37 as follows.

To track the rotation of the gantry 24 relative to the main body of the treatment apparatus, two markers (one of which is not visible in FIG. 1, but is located on the remote side of the gantry 24, in a correspondingly symmetrical position to a marker 30 visible in FIG. 1) may be placed on the gantry head and two markers 32,33 may be placed on the body portion of the treatment apparatus adjacent the main body 22 of the apparatus 16, the markers 30-33 thereby identifying the four corners of a square or rectangle. This arrangement of four markers 30-33 ensures that at all or most times 3 or more markers are in the field of view of a stereoscopic camera system 10 placed opposite the treatment apparatus 16 such as is illustrated in FIG. 1. In the arrangement such as is illustrated in FIG. 1 where the camera planes of the cameras of the stereoscopic camera system 10 are substantially aligned with the plane of rotation of the gantry 24, the markers 30-33 used to track the rotation of the gantry 24 can be individual adhesive stickers made of reflective material stuck on to the surface of the treatment apparatus viewed by the camera system 10. The alignment of camera planes of the cameras of the stereoscopic camera system 10 and the plane of rotation of the gantry 24 simplifies tracking as rotation of the gantry 24 should only cause the apparent positions of the markers 30-33 to vary and not change the apparent size or shape of the markers 30-33.

To maximize the accuracy with which the rotation of the gantry 24 can be monitored, it is advantageous or preferred that the shape and appearance of the markers 30-33 should be such that the centers of the markers 30-33 as they appear in images obtained by the stereoscopic camera system 10 can be easily determined. In these embodiments, this is achieved by utilizing circular markers and processing image data to identify the centers of the imaged markers 30-33.

In the case of the collimator 26, where the camera planes of the cameras of the stereoscopic camera system 10 are substantially aligned with the plane of rotation of the gantry 24, the collimator 26 will be arranged to rotate in a plane which is at right angles to the camera planes of the cameras of the stereoscopic camera system 10. This will mean that as the collimator 26 rotates, different portions of the collimator 26 will be presented in the field of view of the stereoscopic camera system 10. Thus, to track the rotation of the collimator 26, it is advantageous or preferred that the markers 34-37 present on the collimator 26 should be grouped in distinctive patterns so that the presence or absence of particular patterns or markers 34-37 can enable the rotational position of the collimator 26 to be inferred. Thus, for example, the markers 34-37 might be arranged in four groups spaced equally around the circumference of the collimator 26 in slightly different patterns, for example, one group might include or might consist of a single marker 37, one group might include or might consist of two markers 36, 37 immediately adjacent each other, another group might include or might consist of two markers 34, 35 spaced apart and a third group might include or might consist of three markers (not shown in the Figures) on the opposite side of the collimator 26 to one of the other groups. In the illustrated embodiment, this would be the side of the collimator 26 opposite and remote from the pair of spaced apart markers 34, 35. In this way whenever two groups of markers were visible, the identity of the groups could be identified, and the rotational position of the collimator inferred from the apparent position of the visible markers and the identity of the visible groups.

As with the markers 30-33 for tracking the rotation of the gantry 24 it is advantageous or preferable that the shape and appearance of the markers 34-37 should be such that the centers of the markers 34-37 for tracking the rotation of the collimator 26 should also be easily determined. As the rotation of the collimator 26 varies the location, distance and orientation of markers 34-37 on the collimator 26 relative to the camera planes of the cameras of the stereoscopic camera system 10, the shape and appearance of the markers 34-37 will vary as the collimator 26 is rotated. This variance can be reduced by utilizing spherical markers as only the apparent size and not the apparent shape of the markers will vary, hence simplifying the identification of the locations of center of the markers.

Figure 2:
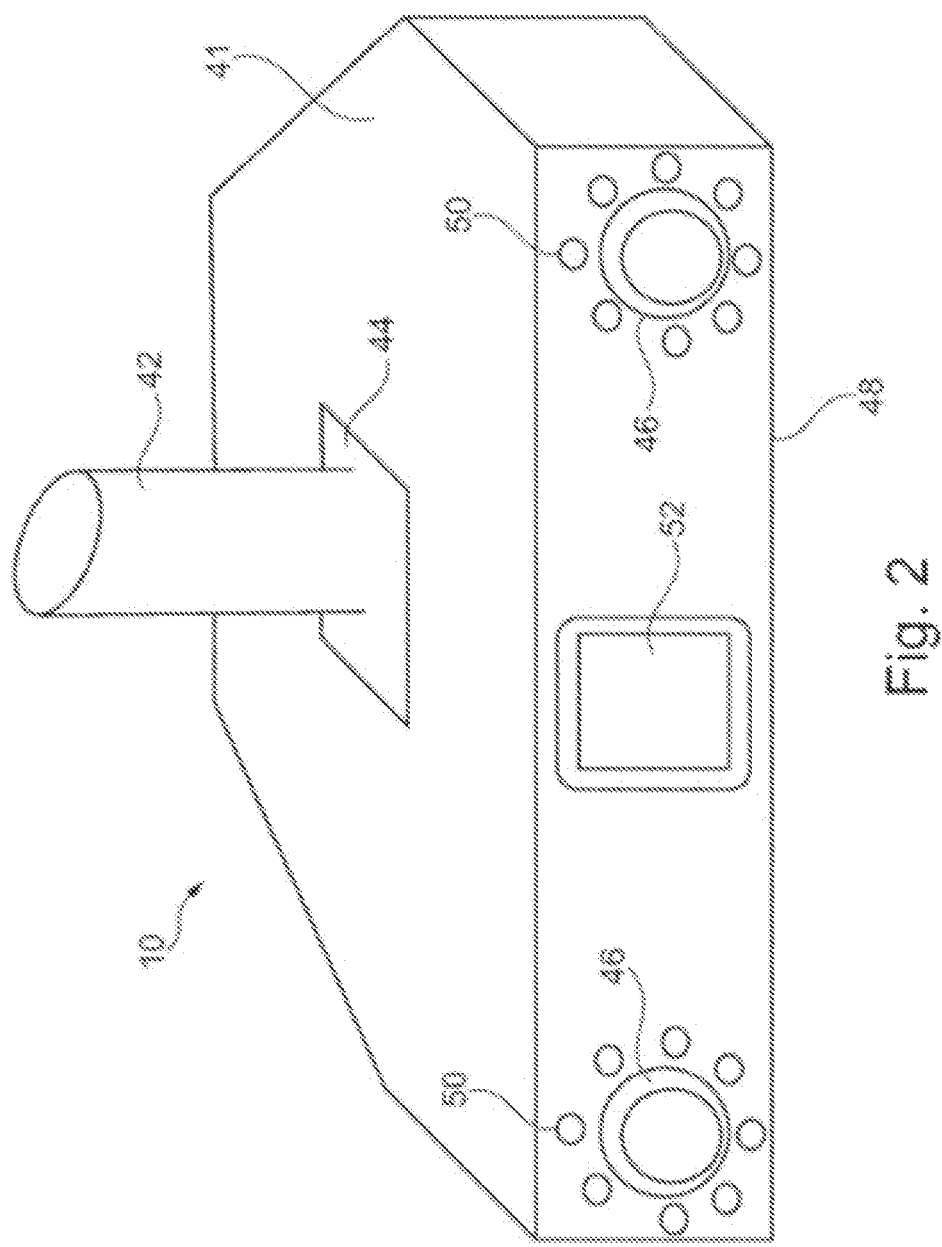
FIG. 2 is a front perspective view of the camera system of the patient monitor of FIG. 1.

FIG. 2 is a front perspective view of the camera system 10 of the patient monitor of FIG. 1.

In these embodiments the camera system 10 includes a housing 41 which is connected to a bracket 42 via a hinge 44. The bracket 42 enables the camera system 10 to be attached in a fixed location to the ceiling of a treatment room whilst the hinge 44 permits the orientation of the camera system 10 to be orientated relative to the bracket 42 so that the camera system 10 is arranged to view a patient 20 on a mechanical couch 18.

A pair of lenses 46 is mounted at either end of the front surface 48 of the housing 41. These lenses 46 are positioned in front of image detectors such as CMOS active pixel sensors or charge coupled devices (not shown) contained within the housing 41. The image detectors are arranged behind the lenses 46 so as to capture images of a patient 20 via the lenses 46.

A set of LED lights 50 is positioned around the outside of the circumference of each of the lenses 46. The LED lights 50 are orientated to illuminate the field of view of the camera system 10 and in particular the retro-reflective markers 30-37 attached to the treatment apparatus 16.

In some embodiments a speckle projector 52 is provided in the middle of the front surface 48 of the housing 41 between the two lenses 46. The speckle projector 52 is arranged to illuminate a patient 20 with a non-repeating speckled pattern of infrared light so that when images of a patient 20 are captured by the two image detectors corresponding portions of captured images can be distinguished. To that end the speckle projector includes a light source such as an LED and a film with a random speckle pattern printed on the film. In use light from the light source is projected via the film and as a result a pattern including or consisting of light and dark areas is projected onto the surface of a patient 20. When images of the projected speckle pattern are captured by the camera system 10 the images can then be processed to determine the positions of a set of points on the surface of the patient and hence the positioning of the patient can be monitored.

Figure 3:
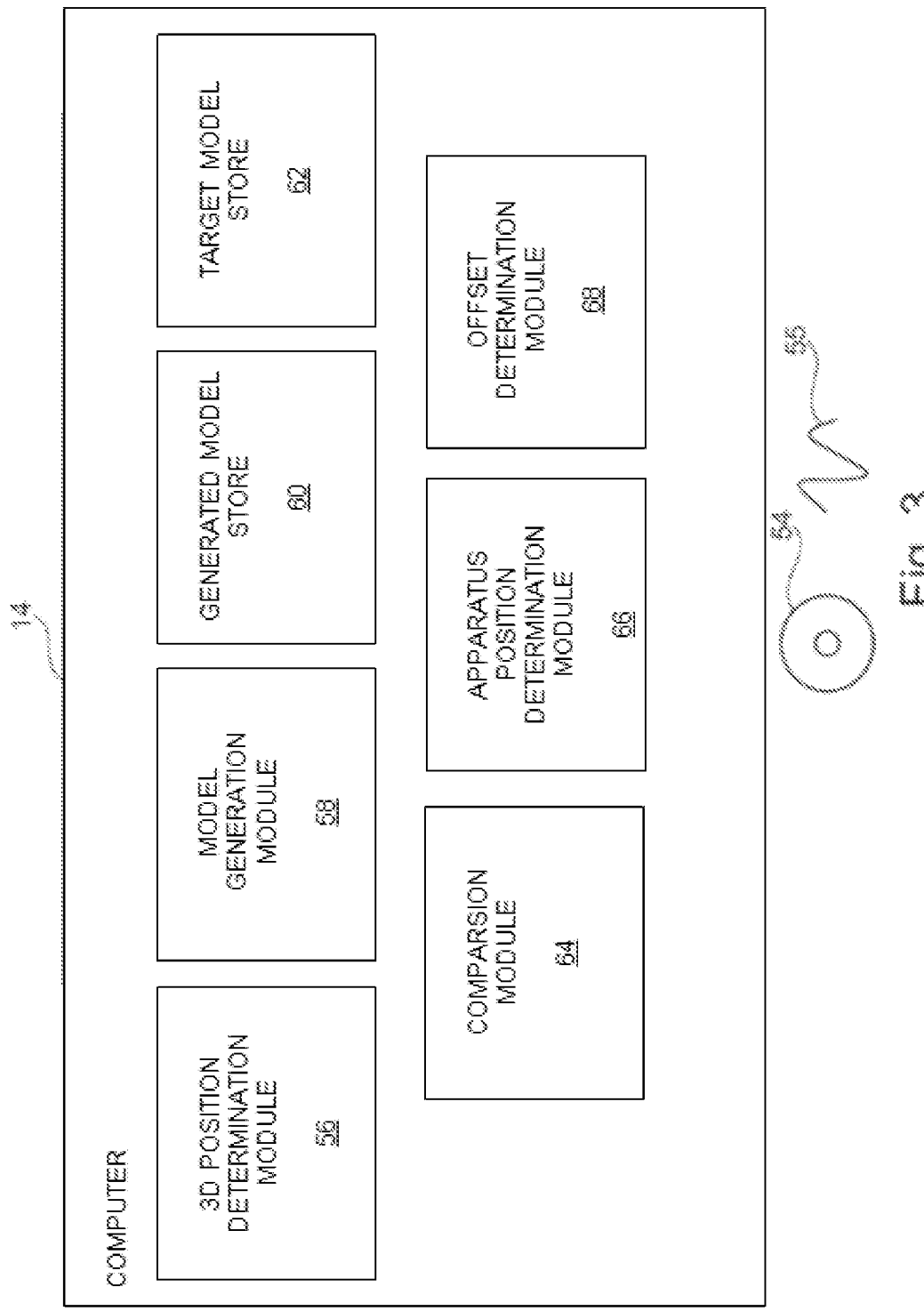
FIG. 3 is a schematic block diagram of the computer system of the patient monitor of FIG. 1.

FIG. 3 is a schematic block diagram of the computer 14 of the patient monitor of FIG. 1.

For the computer 14 to process images received from the stereoscopic cameras 10, the computer 14 is configured by software either provided on a disk 54 or by receiving an electrical signal 55 via a communications network into a number of functional modules 56-68. It will be appreciated that the functional modules 56-68 illustrated in FIG. 3 are purely notional to assist with the understanding of the working of the claimed invention and may not in some embodiments directly correspond with blocks of code in the source code for the software. In some other embodiments the functions performed by the illustrated functional modules 56-68 may be divided between different modules or may be performed by the re-use of the same modules for different functions.

In these embodiments, the functional modules 56-68 include: a 3D position determination module 56 for processing images received from the stereoscopic cameras 10, a model generation module 58 for processing data generated by the 3D position determination module 56 and converting the data into a 3D wire mesh model of an imaged surface; a generated model store 60 for storing a 3D wire mesh model of an imaged surface; a target model store 62 for storing a previously generated 3D wire mesh model; a comparison module 64 for determining rotations and translations required to match a generated model with a target model; an apparatus position determination module 66 for determining the position and orientation of the treatment apparatus and thereby determining the orientation of a path along which the treatment apparatus will generate a beam of radiation; and an offset determination module 68 operable to determine an offset measure on the basis of a transformation determined by the comparison module 64 and the orientation of the radiation path determine by the apparatus position determination module 66.

In use, as images are obtained by the stereoscopic cameras 10, these images are processed by the 3D position determination module 56. This processing enables the 3D position determination module to identify 3D positions of corresponding points in pairs of images on the surface of a patient 20. This is achieved by the 3D position determination module 56 identifying corresponding points in pairs of images obtained by the stereoscopic camera system 10 and then determining 3D positions for those points based on the relative positions of corresponding points in obtained pairs of images and stored data identifying the relative positions of cameras obtaining the images.

Typically, the identification of corresponding points is based on analysis of image patches of around 16×16 pixels. To assist with identifying and matching corresponding patches as has been described the stereoscopic camera system 10 includes a speckle projector 52 arranged to project a random or quasi random speckle pattern onto the patient 20 being imaged so that different portions of the surface of the patient 20 can be more easily distinguished. The size of the speckle pattern is selected so that different patterns will be apparent in different image patches.

The position data generated by the 3D position determination module 56 is then passed to the model generation module 58 which process the position data to generate a 3D wire mesh model of the surface of a patient 20 imaged by the stereoscopic cameras 10. In these embodiments the 3D model includes a triangulated wire mesh model where the vertices of the model correspond to the 3D positions determined by the 3D position determination module 56. When such a model has been determined it is stored in the generated model store 60.

When a wire mesh model of the surface of a patient 20 has been stored, the comparison module 64 is then invoked to determine a matching translation and rotation between the generated model based on the current images being obtained by the stereoscopic cameras 10 and a previously generated model surface of the patient stored in the target model store 62. The determined translation and rotation can then be sent as instructions to the mechanical couch 18 to cause the couch to position the patient 20 in the same position relative to the treatment apparatus 16 as they were when they were previously treated.

During treatment, the stereoscopic camera system 10 continues to monitor the patient 20 and update a generated model of the surface of the patient in the generated model store 60. At the same time the stereoscopic cameras 10 also obtain images of the markers 34-37 attached to the treatment apparatus 16.

The apparatus position determination module 66 is arranged to process images captured by the stereoscopic camera system 10 and identify the portions of the images corresponding to the markers 30-37 attached to the treatment apparatus 16. The apparatus position determination module 66 is then arranged to utilize the identified portions of the images to determine the positioning of the treatment apparatus 16 and thereby determine the orientation of the radiation beam generated by the treatment apparatus. The offset determination module 68 then determines an offset value indicative of the extent of movement of a patient which might adversely affect treatment utilizing the determined orientation of the radiation beam and a comparison between generated model surfaces with the target model stored in the target model store 62 generated by the comparison module 64.

Patient movement can cause a treatment apparatus 16 to irradiate healthy tissue rather than a selected treatment site. However, as previously noted, the absolute extent of movement of a patient is not necessarily a good indicator of the extent to which movement might have a detrimental effect on the application of radiation to a treatment site or is liable to have an adverse impact on a patient.

Figure 4:
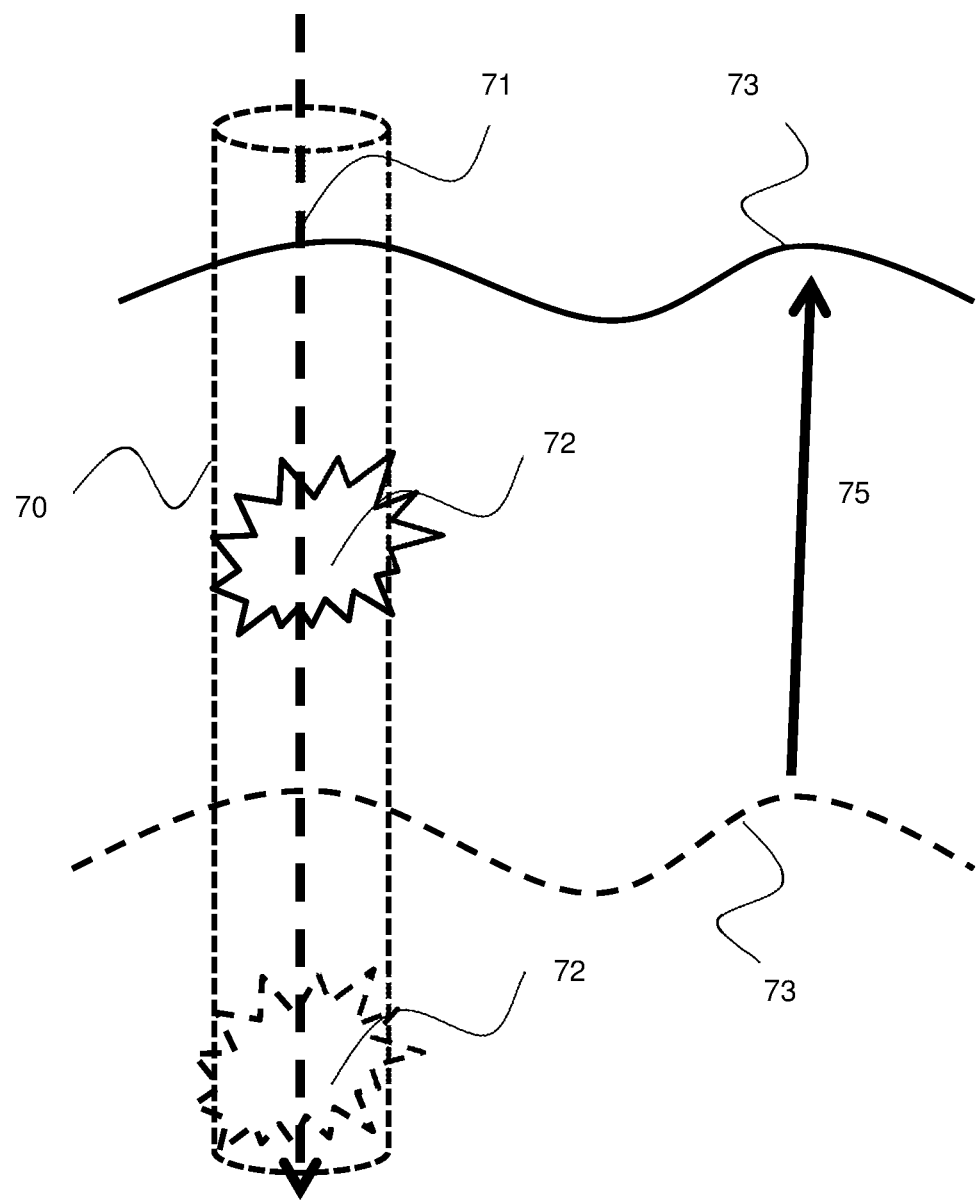
FIGS. 4-7 are schematic illustrations of the passage of a radiation beam through a patient.
Figure 5:
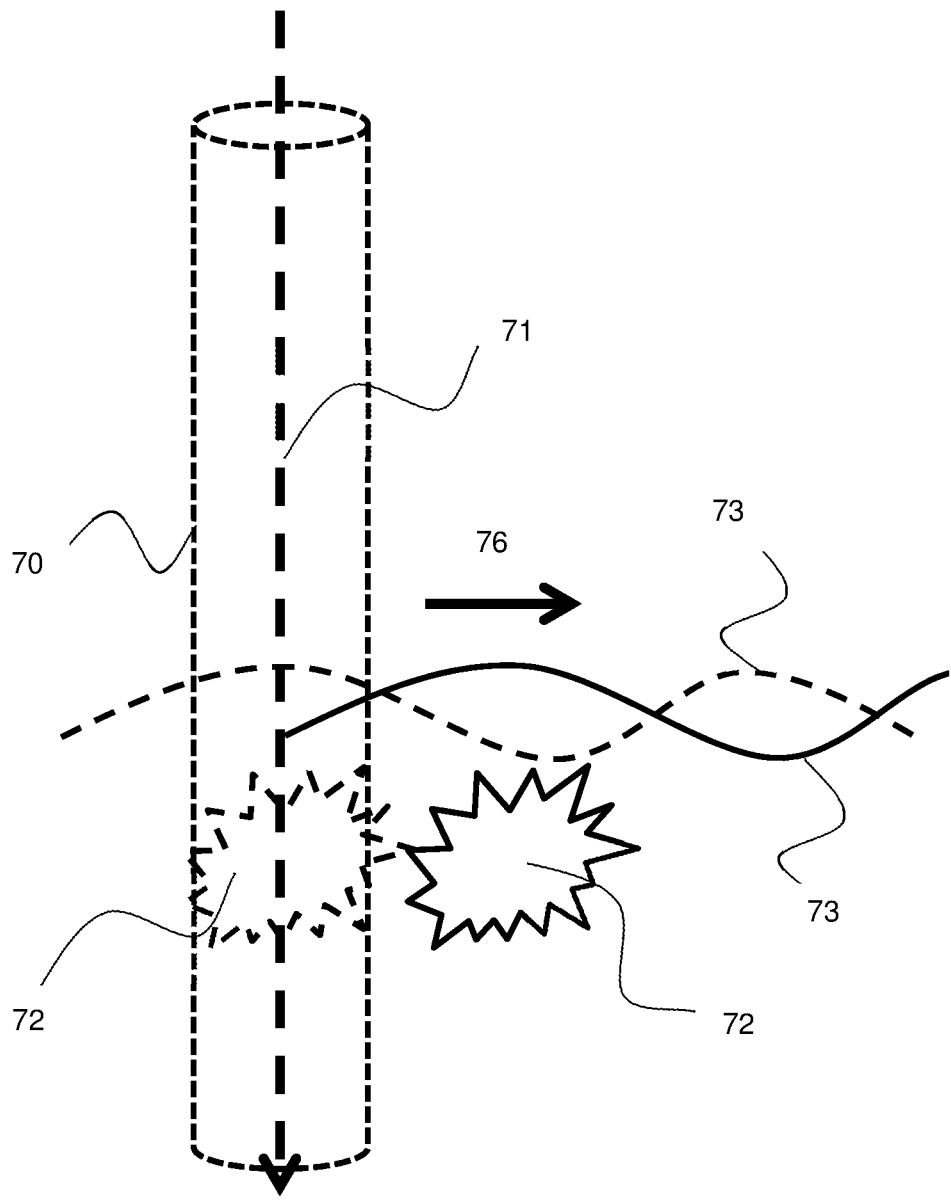

FIGS. 4 and 5 are schematic illustrations of the passage of a radiation beam through a patient illustrating the relationship between beam orientation and patient movement and misapplication of radiation.

In the Figures a radiation beam 70 oriented in a direction shown by arrow 71 is targeted towards a target tumor 72. Due to patient movement, the actual location of the target tumor and the surface of the patient 73 moves from a first position (shown in dotted outline in FIGS. 4 and 5) to a new position (shown in FIGS. 4 and 5). The motion in the case of FIG. 4 is motion substantially parallel to the path of the radiation beam. Whereas the motion illustrated in FIG. 5 is normal to the path of the radiation beam. The extent and direction of movement is shown by arrows 75 and 76.

As is shown in FIGS. 4 and 5 the absolute extent of the movement shown by the length of arrow 75 in FIG. 4 is greater than the extent of movement shown by the length of arrow 76 in FIG. 5. However, as the direction of motion in FIG. 4 is substantially parallel to the direction of the radiation beam 70, then although the absolute extent of movement illustrated in FIG. 4 is greater than that shown in FIG. 5, the smaller motion illustrated in FIG. 5 causes the radiation beam 70 no longer to irradiate the target tumor 72 whereas in FIG. 4 the target tumor 72 is still irradiated by the radiation beam 70.

Monitoring the surface of a patient and determining a transformation required to match a generated model of the surface of a patient 20 with a model of a patient utilized to select a treatment site enables the monitoring system to identify the extent and direction of movement of the surface 73 of a patient and by implication possible movement of an associated target site 72.

In these embodiments when the offset determination module 68 receives data identifying the determined orientation of the radiation beam and the determined transformation required to match a generated model surface with a target model stored in the target model store 62, the offset determination module 68 determines an offset value indicative of the extent of movement of a patient which might adversely affect treatment.

A simple measurement would be one based upon the direction and magnitude of a calculated transformation required to match a current generated model surface with a target model calculated by the comparison module 64 and the determined orientation of the radiation beam generated by the treatment apparatus calculated by the apparatus position determination module 66.

Thus for example one measure could be a determination of a measurement in the form of $|\alpha| \sin \theta$ where $|\alpha|$ is the magnitude of a vector $\alpha$ corresponding to the transformation for best or better fit between a current generated surface stored in the generated model store 60 and a stored target model surface stored in the target model store 62 determined by the comparison module 64 and $\theta$ is the angle between the vector $\alpha$ determined by the comparison module 64 and a vector aligned with the orientation of the radiation beam as determined by the apparatus position determination module 66.

In some other embodiments, rather than a simple offset value calculated directly from the vector corresponding to the transformation for best or better fit between a current generated surface and a stored model and a determined orientation of a radiation beam 70, a more complex determination of an offset value could be made.

Thus, for example, in some embodiments, the shape and volume of a target tumor 72 could be modelled. An offset value could then be determined on the basis of an estimated extent of intersection of a radiation beam with the target tumor, based on the transformation and the determined orientation of a radiation beam.

In such embodiments, the motion of a tumor 72 could be assumed to follow a path based on the motion of the detected surface of a patient. Such motion could either be assumed to place a tumor in a fixed position relative to a monitored surface or alternatively where additional information about the movement of the tumor was available, a more complex model of the motion of a tumor 72 could be used and an offset value could be determined utilizing such a model.

Many radiation treatment apparatus include multi-leaf collimators enabling the shape of a radiation beam 70 to be varied. Where a treatment apparatus 16 includes a multi-leaf collimator or other methods for varying the shape of a radiation beam 70 is provided, the determination an estimated extent of intersection of a radiation beam 70 with the target tumor 72 may be based upon an estimated intersection of the target tumor based on an estimated projection of a radiation beam onto the tumor 72 where the shape of the estimated projection is based upon the arrangement of the multi-leaf collimator when radiation is applied to a patient.

Having determined the offset value, the offset value could be displayed on a screen of the computer 14 to inform a technician of the extent of adverse movement of the patient 20. Alternatively, or in addition the computer 14 could be arranged to compare the calculated offset with a threshold value and trigger a warning or alternatively halt treatment if the calculated offset exceeds the threshold.

In some other embodiments rather than the offset determination module 68 utilizing the transformation determined by the comparison module and data indicative of a current position of a treatment apparatus to determine an offset value and displaying that value or utilizing the value to trigger a warning or halt treatment, the offset determination module could instead utilize the transformation determined by the comparison module 64 and data indicative of a current position of a treatment apparatus to model the passage of a radiation beam through the body of a patient to determine if a patient has moved out of position in a manner which is likely to be detrimental to the patient. Such a model could, in addition to determining whether patient movement is likely to cause a treatment apparatus 16 to fail to irradiate a target tumor, might also enable the offset determination module 68 to determine whether a treatment apparatus was liable to irradiate critical tissue and provide a warning or halt treatment if that was liable to occur.

Figure 6:
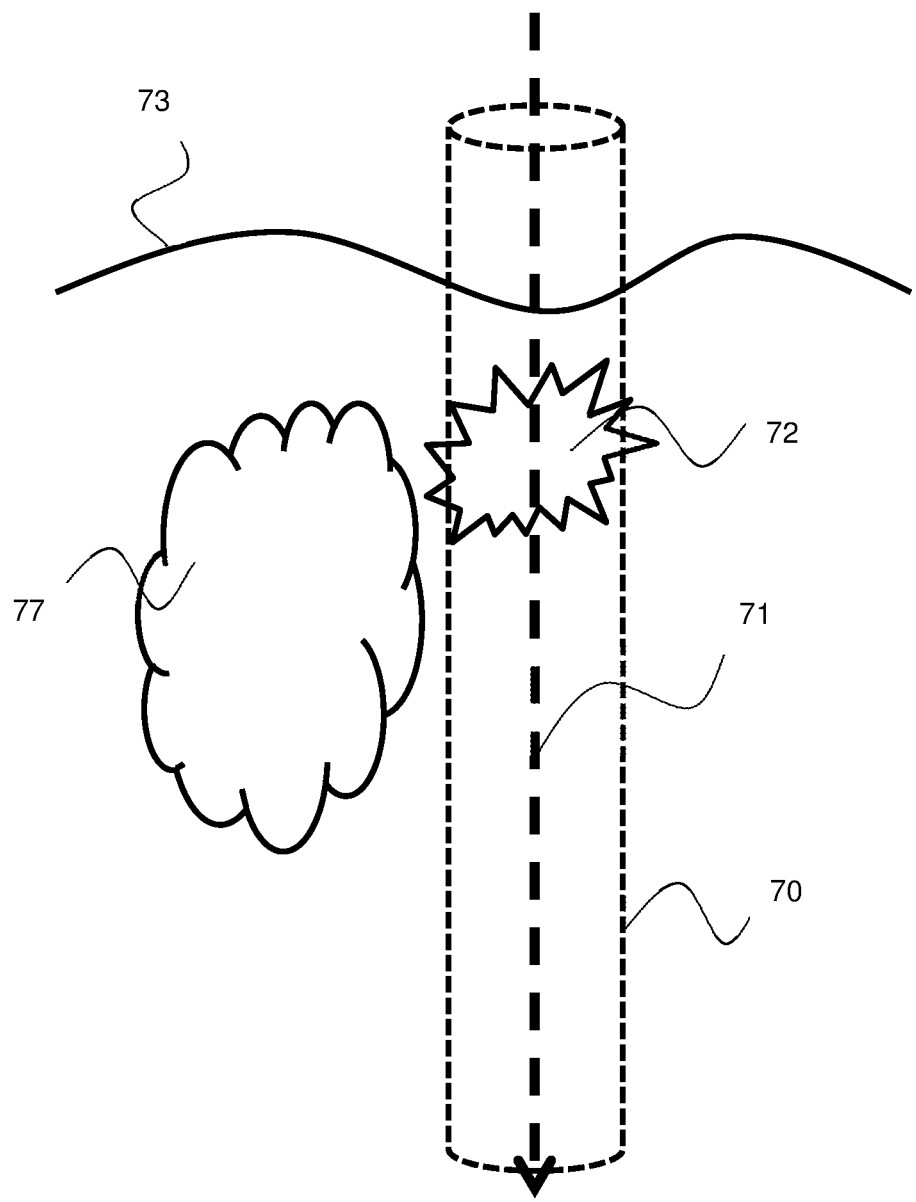

Thus, for example as shown in FIG. 6, a treatment plan might be based upon the images identifying that a target tumor 72 is located in a particular position relative to the surface 73 of a patient. In this example the target tumor is shown adjacent critical tissue 77. When planning treatment it is assumed that a radiation beam 70 is to be applied along a radiation path 71 so as to irradiate the target tumor 72 without irradiating the critical tissue 77.

Figure 7:
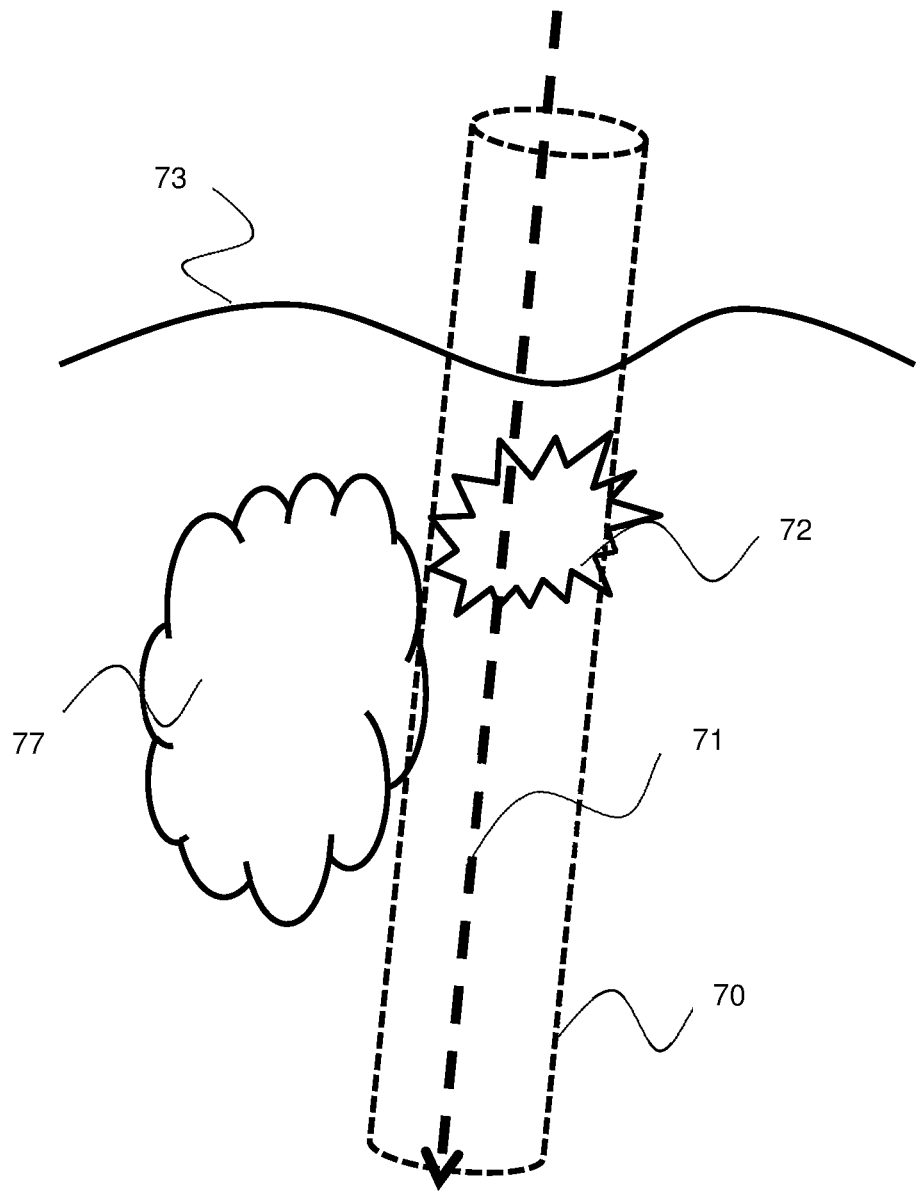

Subsequently during treatment, as shown in FIG. 7, the surface 73 of a patient might be determined, based on a comparison between a generated model stored in the generated model store 60 and a target model stored in the target model store 62, to have moved slightly. In addition, the identified position of the treatment apparatus 16 might be identified so as to irradiate the patient at a slight angle compared with the expected position of the treatment apparatus 16 in the treatment plan.

In such circumstance, it may be the case that an offset value determined on the basis of a transformation required to match the generated model stored in the generated model store 60 and a target model stored in the target model store 62 is such to indicate that an acceptable proportion of the target tumor 72 still falls within the expected path of the radiation beam 70. However, as indicated in FIG. 7 it may, however, be the case that the combination of patient movement and treatment apparatus misalignment causes the radiation beam 70 to irradiate part of the critical tissue 77.

As an addition or an alternative to calculating an offset value on the basis of a determined transformation for matching a modelled surface of a patient to a stored model surface and data utilized to determine the orientation of radiation beam, in some embodiments the determined orientation and calculated offset could be utilized to model the passage of radiation through a patient and determine, in addition to whether the radiation beam irradiates a tumor target site, whether or not as a result of patient movement and/or variations of beam orientation the radiation beam will irradiate critical tissue and warnings and/or the halting of treatment could be triggered utilizing such a model.

Although in the above described embodiment, a monitoring system has been described in which a stereoscopic camera system 10 projects a pattern of light onto the surface of a patient to identify corresponding portions of a patient 20 appearing in stereoscopic images captured by the camera system 10, it will be appreciated that other forms of patient monitor could be used.

Thus, for example, in some other embodiments the position of a patient 20 could be monitored by projecting a pattern of structured light such a grid pattern or a line of laser light or other predefined pattern of light onto the surface of a patient and monitoring how the pattern was deformed when projected onto the surface of the patient.

Alternatively, in some other embodiments the position of a patent 20 and/or the orientation of a treatment apparatus 16 could be determined by monitoring the patient 20 and/or the treatment apparatus 16 using a time of flight camera where light (typically infra-red laser light) is projected onto the surface of an object being monitored and the distance between the camera and the object is determined by the time taken between the activation of the light and receipt by the camera of light reflected from a surface.

Although in the above described embodiment a stereoscopic camera system 20 is used to monitor the position of a patient 20 and the position and orientation of a treatment apparatus 16, it will be appreciated that position and orientation of a treatment apparatus 16 could be monitored in other ways. Thus, for example, feedback from motion detectors, stepper motors or servos within the treatment apparatus 16 could be used to determine the position and orientation of a treatment apparatus 16.

Alternatively, rather than monitoring the position and orientation of a treatment apparatus 16 an offset measure could be derived based upon an assumed position and orientation of a treatment apparatus at a particular point in time based upon a treatment plan for treating a patient 20.

Although some embodiments described with reference to the drawings include computer apparatus and processes performed in computer apparatus, some other embodiments also extend to computer programs, particularly computer programs on or in a carrier, adapted for putting some embodiments into practice. The program may be in the form of source or object code or in any other form suitable for use in the implementation of the processes according to some embodiments. The carrier can be any entity or device capable of carrying the program.

For example, the carrier may include a storage medium, such as a ROM, for example a CD ROM or a semiconductor ROM, or a magnetic recording medium, for example a floppy disc or hard disk. Further, the carrier may be a transmissible carrier such as an electrical or optical signal which may be conveyed via electrical or optical cable or by radio or other device. When a program is embodied in a signal which may be conveyed directly by a cable or other device, the carrier may be constituted by such cable or other device. Alternatively, the carrier may be an integrated circuit in which the program is embedded, the integrated circuit being adapted for performing, or for use in the performance of, the relevant processes.

While the subject matter has been described in detail with reference to exemplary embodiments thereof, it will be apparent to one skilled in the art that various changes can be made, and equivalents employed, without departing from the scope of the invention. All related art references discussed in the above Background section are hereby incorporated by reference in their entirety.

What is claimed is:

1. A monitoring system for monitoring the positioning of a patient relative to a treatment apparatus operable to deliver radiation along a radiation path, the monitoring system comprising:
   a model generation module operable to generate a model of a surface of the patient being monitored;
   a target model store operable to store a model of a target surface;
   a comparison module operable to determine a transformation required to match a model of the surface of the patient generated by the model generation module with a model of the target surface stored in the target model store; and
   an offset determination module operable to utilize the transformation determined by the comparison module and data indicative of a current position of the treatment apparatus to determine an offset value indicative of the offset of the surface of the patient relative to an axis corresponding to a determined current radiation path for radiation generated by the treatment apparatus applied to the patient; and
   wherein the offset value is determined as the modulus of a vector corresponding to the calculated transformation for matching the generated model of a surface with the model of the target surface multiplied by the sine of an angle corresponding to the angle between the vector and the determined current radiation path of radiation generated by the treatment apparatus.

2. The monitoring system in accordance with claim 1, wherein the monitoring system is arranged to monitor the position and orientation of the treatment apparatus and determine the current radiation path of radiation generated by the treatment apparatus.

3. The monitoring system in accordance with claim 1, wherein the monitoring system is operable to receive data from the treatment apparatus and the monitoring system is arranged to determine the position and orientation of the treatment apparatus and determine the current radiation path of radiation generated by the treatment apparatus on the basis of received data.

4. The monitoring system in accordance with claim 1, wherein the monitoring system is arranged to infer an axis corresponding to the current radiation path of radiation generated by the treatment apparatus from a treatment plan identifying the positions and orientations from which the patient is to be irradiated.

5. The monitoring system in accordance with claim 1, wherein the offset determination module is operable to determine an offset value indicative of the offset between the centroid of a generated model surface and a target surface in a direction normal to the axis corresponding to the current radiation path.

6. The monitoring system in accordance with claim 1, wherein the offset determination module is operable to determine an offset value indicative of the degree of overlap between a target region and a generated radiation beam.

7. The monitoring system in accordance with claim 1, wherein the offset determination module is arranged to utilize the transformation determined by the comparison module and data indicative of a current position of the treatment apparatus to model the passage of the radiation beam through the body of the patient to determine if the patient has moved out of position in a manner which is likely to be detrimental to the patient.

8. The monitoring system in accordance with claim 1, further including a camera system operable to image the surface of the patient being monitored, wherein the model generation module is operable to process images obtained by the camera system to generate a model of the surface of the patient being monitored.

9. The monitoring system in accordance with claim 8, wherein the camera system is operable to image a pattern of light projected onto the surface of the patient.

10. The monitoring system in accordance with claim 9, wherein the pattern of light includes structured light and the model generation module is operable to process images of the patient obtained by the camera system and generate a model of the surface of the patient being monitored on the basis of the deformation of the projected pattern of light onto the surface of the patient.

11. The monitoring system in accordance with claim 9, wherein the camera system includes a stereoscopic camera system and the pattern of light includes a pseudo random speckle pattern, wherein the model generation module is operable to process images of the patient obtained by the stereoscopic camera system to identify matches between portions of stereoscopic images corresponding to points on the surface of the patient being monitored and utilize the matched portions to generate a model of the surface of the patient being monitored.

12. The monitoring system in accordance with claim 9, wherein the model generation module is operable to generate a model of the surface of the patient being monitored on the basis of a determination of the relative distance between the patient and the camera system based on the relative timing of illumination of portions of the patient by the light projected onto the surface of the patient and receipt of images of the projected light.

13. The monitoring system in accordance with claim 8, wherein the camera system is operable to obtain images of the treatment apparatus and process the images to determine the orientation of an axis corresponding to the current radiation path.

14. A non-transient computer readable medium storing instructions for monitoring the positioning of a patient relative to a treatment apparatus operable to deliver radiation along a radiation path which when interpreted by a programmable computer cause the computer to:

generate a model of a surface of the patient being monitored;

store a model of a target surface;

determine a transformation required to match a model of the surface of the patient generated by the model generation module with a model of the target surface stored in the target model store; and utilize the transformation determined by the comparison module and data indicative of a current position of the treatment apparatus to determine an offset value indicative of the offset of the surface of the patient relative to an axis corresponding to a determined current radiation path for radiation generated by the treatment apparatus applied to the patient; and wherein the offset value is determined as the modulus of a vector corresponding to the calculated transformation for matching the generated model of a surface with the model of the target surface multiplied by the sine of an angle corresponding to the angle between the vector and the determined current radiation path of radiation generated by the treatment apparatus.

15. The non-transient computer readable medium storing instructions in accordance with claim 14, wherein the instructions cause the computer to infer an axis corresponding to the current radiation path of radiation generated by the treatment apparatus from a treatment plan identifying the positions and orientations from which the patient is to be irradiated.

16. The non-transient computer readable medium storing instructions in accordance with claim 14, wherein the instructions cause the computer to determine an offset value indicative of the offset between the centroid of a generated model surface and a target surface in a direction normal to the axis corresponding to the current radiation path.

* * * * *